(12) United States Patent
Wang et al.

(10) Patent No.: US 11,098,278 B2
(45) Date of Patent: Aug. 24, 2021

(54) PRETREATMENT METHOD FOR LC-MS DETECTING METABOLOMICS OF ASPERGILLUS FLAVUS

(71) Applicant: OIL CROPS RESEARCH INSTITUTE, CHINESE ACADEMY OF AGRICULTURAL SCIENCES, Hubei (CN)

(72) Inventors: Xiupin Wang, Hubei (CN); Peiwu Li, Hubei (CN); Huali Xie, Hubei (CN); Xuefang Wang, Hubei (CN); Qi Zhang, Hubei (CN); Xiaoxia Ding, Hubei (CN); Wen Zhang, Hubei (CN); Liangxiao Zhang, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 30 days.

(21) Appl. No.: 16/594,081

(22) Filed: Oct. 7, 2019

(65) Prior Publication Data
US 2020/0032200 A1    Jan. 30, 2020

Related U.S. Application Data

(63) Continuation of application No. PCT/CN2018/081793, filed on Apr. 4, 2018.

(30) Foreign Application Priority Data

Apr. 6, 2017    (CN) .................... 201710220934.X (51) Int. Cl.
| C12N 1/06 | (2006.01) |
| C12N 1/14 | (2006.01) |
| C12N 1/00 | (2006.01) |
| G01N 1/42 | (2006.01) |

(52) U.S. Cl.
CPC .............. *C12N 1/06* (2013.01); *C12N 1/005* (2013.01); *C12N 1/14* (2013.01); *G01N 1/42* (2013.01)

(58) Field of Classification Search
None
See application file for complete search history.

(56) References Cited

PUBLICATIONS

Arroyo-Manzanares, Natalia et al. Use of UHPLC high-resolution Orbitrap mass spectrometry to investigate the genes involved in the production of secondary metabolites in Aspergillus flavus. Food Additives & Contaminants: Part A, 2015. (Year: 2015).*
Villas-Boas, Silas et al. Cold glycerol-saline: The promising quenching solution for accurate intracellular metabolite analysis of microbial cells. Analytical Biochemistry 370 (2007) 87-97. (Year: 2007).*
Kavier Duportet, et al., "The biological interpretation of metabolomic data can be misled by the extraction method used," Metabolomics, vol. 8, Jun. 2011, pp. 410-421.
Kathleen F Smart, et al., "Analytical platform for metabolome analysis of microbial cells using methyl chloroformate derivatization followed by gas chromatography-mass spectrometry," Nature protocols, vol. 5, Sep. 2010, pp. 1709-1718.

* cited by examiner

*Primary Examiner* — Nghi V Nguyen
(74) *Attorney, Agent, or Firm* — JCIP Global Inc.

(57) ABSTRACT

The invention belongs to the field of chemical analysis and detection, and specifically relates to a pretreatment method for LC-MS detecting metabolomics of Aspergillus flavus. The method includes: culturing a strain of Aspergillus flavus; quenching the Aspergillus flavus; disrupting the cell membrane of Aspergillus flavus, and extracting a metabolome. The invention adopts a cold glycerol buffer solution combined with a rapid filtration method for quenching, and a MeOH/DCM/ACN/EA/HCOOH mixture is used as an metabolome extract, thereby achieving the object of efficiently extracting different polar compounds, and metabolome compound coverage is high; pretreatment of the cell metabolomics of Aspergillus flavus by the method of the invention can ensure the repeatability and stability of the metabolomics analysis method and reduce the false positive of the test results.

9 Claims, 7 Drawing Sheets

PRETREATMENT METHOD FOR LC-MS DETECTING METABOLOMICS OF ASPERGILLUS FLAVUS

CROSS-REFERENCE TO RELATED APPLICATION

This application is a continuation of international PCT application serial no. PCT/CN2018/081793, filed on Apr. 4, 2018, which claims the priority benefit of Chinese application no. 201710220934.X, filed on Apr. 6, 2017. The entirety of each of the above-mentioned patent applications is hereby incorporated by reference herein and made a part of this specification.

BACKGROUND OF THE INVENTION

Field of the Invention

The invention relates to the field of chemical analysis and detection, and specifically relates to a pretreatment method for detecting metabolomics of Aspergillus flavus by LC-MS.

Description of Related Art

The metabolome of Aspergillus flavus is an indispensable part of systematic biology research on the genome, transcriptome, and toxigenic mechanism of Aspergillus flavus, but the current detection method of the metabolome of Aspergillus flavus is far from meeting the needs of systematic biology research. Poor pretreatment methods severely affect the coverage of the metabolome of Aspergillus flavus, and metabolic compounds with low levels and important markers are often not detected.

The study on the metabolome of Aspergillus flavus belongs to the field of microbial metabolomics research. Microbial metabolomics is a study of microorganisms and aims to study all small molecular weight metabolomes inside and outside the cell at some point in the cell growth cycle. Microorganisms are the most metabolized organisms on the earth. The enzymes in the cells are active and the metabolomes are rapidly converted. Therefore, whether the culture conditions of the samples are stable and the processing methods of the samples can significantly affect the accuracy of the analysis results.

At present, microbial metabolomics is at the initial stage of its development. Microbial metabolomics has been successfully applied to new drug development, mutant screening, microbial metabolic engineering, microbial degradation of pollutants, and the pathological relationship between microorganisms and hosts, etc. due to a series of advantages such as simple system, rich genomic data, and comprehensive understanding of metabolic networks and physiological characteristics of the microorganisms themselves. Metabolomics studies on Aspergillus flavus have just started. Roze et al. used metabolomics to compare the metabolome of a wild-type strain of Aspergillus flavus and the strain of VeA mutations, and found changes in some volatile components, revealing the function of VeA in regulating branching amino acid and ethanol metabolism.

Therefore, the invention of a high-efficiency pretreatment method and a broad coverage detection method for the metabolome of Aspergillus flavus is of great significance for further study on the physiological metabolism of Aspergillus flavus and related environmental response mechanisms.

SUMMARY OF THE INVENTION

The invention is directed to the deficiencies of the prior art, and aims to provide a pretreatment method for detecting metabolomics of Aspergillus flavus by LC-MS.

In order to achieve the above object, the technical solution adopted by the invention is:

A pretreatment method for detecting metabolomics of Aspergillus flavus by LC-MS, including the following steps:

(1) A strain of Aspergillus flavus is cultured: after Aspergillus flavus is cultured in a solid medium, spores are washed from the solid medium with a sterile water and then the spores are inoculated into a liquid medium for propagation to obtain a sample of Aspergillus flavus;

(2) Aspergillus flavus is quenched: a sample of Aspergillus flavus obtained from step (1) is added to a cold glycerol buffer solution quenching agent, rapidly mixed and vortexed, homogenized, then cooled under low temperature conditions, and then rapidly filtered a mixture by vacuum filtration, and a solid sample is collected, and the solid sample is freeze-dried to obtain a cell sample of Aspergillus flavus;

(3) A cell membrane of Aspergillus flavus is disrupted and a metabolome is extracted: the cell sample of Aspergillus flavus obtained by freeze-drying in step (2) is disrupted and an extraction process is performed using a metabolome extract, and then the sample is centrifuged and membrane-filtered to obtain a metabolome extraction solution for the metabolomics of Aspergillus flavus analysis by LC-MS detection.

In the above solution, the method for culturing the strain of Aspergillus flavus is as follows: Aspergillus flavus is inoculated on a Czapek solid medium and cultured at 18 to 38° C. for 8 to 12 days, and the spores are washed from the solid medium with sterile water. Then, the spores are inoculated into a Sabouraud's liquid medium and cultured on a constant temperature shaker for 5 to 7 days to obtain a sample of Aspergillus flavus.

In the above solution, the sterile water contains Tween-80 having a volume fraction of 0.05% to 0.2%, and the inoculum of the Aspergillus flavus in the Sabouraud's liquid medium is $1\times10^5$ to $5\times10^5$ cells/mL; the culture temperature of the constant temperature shaker is 25 to 30° C., and the rotating speed of the shaker is 150 to 250 r/min.

In the above solution, the cold glycerol buffer solution quenching agent in step (2) is prepared by mixing glycerol and NaCl solution in a volume ratio of 1:1 to 2:1.

In the above solution, the cold glycerol buffer solution quenching agent in step (2) is pre-cooled to −30° C. or less for use, and the concentration of the NaCl solution is 10 to 15 g/L.

In the above solution, the volume ratio of the sample of Aspergillus flavus and the cold glycerol buffer solution quenching agent in step (2) is 1:4 to 1:6.

In the above solution, the cooling under low temperature conditions in step (2) is as follows: the mixture is cooled at −20 to −40° C. for 3 to 5 minutes.

In the above solution, the freeze-drying time in step (2) is 8 to 12 hours.

In the above solution, the metabolome extract of step (3) is formed by mixing methanol (MeOH), DCM (dichloromethane), ACN (acetonitrile), EA (ethyl acetate), and HCOOH (formic acid) in a volume ratio of 20 to 30:20 to 30:20 to 30:20 to 30:1 to 2.

In the above solution, in step (3), the metabolome extract is added in an amount of 1 to 2 mL based on 100 to 200 mg of the cell sample of Aspergillus flavus.

In the above solution, the cell is disrupted and the metabolome is extracted by ultrasound in step (3), the ultrasonic power is 240 to 300 W, and the ultrasonic disruption extraction time is 15 to 20 min.

In the above solution, the centrifugal speed of step (3) is 8000 to 10000 rpm, and the centrifugal time is 5 to 10 min.

In the above solution, the membrane-filtered membrane of step (3) is a 0.22 μm organic membrane.

In the above solution, the method further includes step (4): the metabolomics of Aspergillus flavus is analyzed, specifically: the metabolome extraction solution obtained in step (3) is subjected to an HPLC-MS system for analysis and detection, and then the metabolomics of Aspergillus flavus is analyzed according to the obtained spectrum; the mass spectrometric conditions the HPLC-MS system analysis and detection in step (4) are: an ion source heating temperature of 250 to 350° C., a spray voltage of 3.5 to 4 Kv in positive ion mode, 3.0 to 3.5 Kv in negative ion mode, a sheath gas of 30 to 40 Arb, an auxiliary gas of 5 to 10 Arb, and an ion transfer capillary temperature of 300 to 320° C.

In the invention, the cell metabolome compound of Aspergillus flavus is placed in the HPLC-MS system for analysis, and after the raw data is collected by the analysis and detection of the HPLC-MS system, the raw data is respectively peak-aligned, extracted, and a metabolome library search is performed to obtain the raw peak table, and then a metabolome analysis is performed; extraction of peak tables of mass spectrometry raw data files and metabolome characterization are implemented by SIEVE 3.0.

THE BENEFICIAL EFFECTS OF THE INVENTION (1) The invention uses a cold glycerol buffer solution combined with a rapid filtration method to quench the cells of Aspergillus flavus, which can not only rapidly quench cell enzyme activity, but also freezes the physiological metabolism time at the time of sampling to obtain accurate metabolome data; moreover, the quenching method of the invention does not readily damage the cell membrane of Aspergillus flavus, and can maintain the integrity of the cell tissue to a greater extent, and has the advantages of repeatability and accuracy;

(2) The invention uses a mixture of MeOH/DCM/ACN/EA/HCOOH as an metabolome extract to achieve the object of efficiently extracting different polar compounds, and metabolome compound coverage is high;

(3) The invention adopts an ultrasonic disruption extraction process and completes cell disruption and metabolome compound extraction by one-step synchronization, which simplifies the pre-treatment process and saves labour and time;

(4) Pretreatment of the cell metabolomics of Aspergillus flavus by the method of the invention can ensure the repeatability and stability of the metabolomics analysis method and reduce false positive of the test results.

BRIEF DESCRIPTION OF THE DRAWINGS

The accompanying drawings are included to provide a further understanding of the invention, and are incorporated in and constitute a part of this specification. The drawings illustrate examples of the invention and, together with the description, serve to explain the principles of the invention.

FIGS. 1a~1b are mass spectrometry chromatogram of the metabolome of Aspergillus flavus cultured at 18° C., wherein FIG. 1a shows the positive ion acquisition mode and FIG. 1b shows the negative ion acquisition mode.

FIGS. 2a~2b show the mass spectrometry chromatogram of the metabolome of Aspergillus flavus cultured at 28° C., wherein FIG. 2a shows the positive ion acquisition mode and FIG. 2b shows the negative ion acquisition mode.

FIGS. 3a~3b are mass spectrometry chromatogram of the metabolome of Aspergillus flavus cultured at 38° C., wherein FIG. 3a shows the positive ion acquisition mode and FIG. 3b shows the negative ion acquisition mode.

FIGS. 4a~4c show the results of three different quenching modes under a laser confocal microscope, wherein FIG. 4a shows liquid nitrogen quenching, FIG. 4b shows cold methanol quenching, and FIG. 4c shows cold glycerol-buffer solution combined with rapid filtration quenching.

DETAILED DESCRIPTION OF THE EMBODIMENTS

In order to better understand the invention, the content of the invention is further clarified below with reference to examples, but the content of the invention is not limited to the following examples.

Example 1

A pretreatment method for the metabolome analysis of Aspergillus flavus cultured in a Czapek solid medium at 18° C., including the following steps:

(1) Culture of strain of Aspergillus flavus: Aspergillus flavus was inoculated on a Czapek solid medium, and after 8 to 12 days of incubation at 18° C., the spores were washed from the medium using sterile water (containing 0.05 to 0.2% Tween-80); then, the suspension of Aspergillus flavus spores was inoculated in a Sabouraud's liquid medium, the inoculum reached $1\times10^5$ to $5\times10^5$/ml, and the culture flask was placed on a 25 to 30° C. constant temperature shaker (150 to 250 r/min) to culture for 5 to 7 days to obtain a sample of Aspergillus flavus;

(2) Quenching of Aspergillus flavus cells using a cold glycerol buffer solution combined with rapid filtration:

1. A sample of Aspergillus flavus was rapidly transferred to a centrifuge tube containing a cold glycerol buffer solution quenching agent (formed by mixing glycerol and NaCl solution in a 1:1 volume ratio, <−30° C., NaCl solution concentration 13.5 g/L), and the sample to quenching agent volume ratio was maintained between 1:4;

2. The mixture of the sample and the cold glycerol buffer solution quenching agent was rapidly vortexed for 8 to 12 seconds, homogenized, and then the mixture was cooled at −20° C. for 3 to 5 minutes;

3. The mixture was rapidly filtered by vacuum filtration, and the solid sample was collected and freeze-dried for 8 hours after freezing;

(3) Cell disruption and metabolome extraction of Aspergillus flavus: 1 to 2 mL metabolome extract was added to 100 to 200 mg of the freeze-dried spore sample of step (2), disrupted by ultrasound and extracted for 15 min, ultrasonic power was 240 W, centrifuged at 8000 to 10000 rpm for 5 to 10 min, filtered via a 0.22 μm organic membrane to obtain a metabolome extract; the component distribution ratio of the metabolome extract was: volume ratio of MeOH/DCM/ACN/EA/HCOOH=24.5/24.1/24.7/25.7/1;

(4) Analysis of metabolome of Aspergillus flavus: the metabolome extract obtained in step (4) was analyzed and detected by an HPLC-MS system, and the mass spectrometry conditions were: an ion source heating temperature of 250 to 350° C., a spray voltage of 3.5 to 4 Kv in positive ion mode, 3.0 to 3.5 Kv in negative ion mode, a sheath gas of 30 to 40 Arb, an auxiliary gas of 5 to 10 Arb, and an ion transfer capillary temperature of 300 to 320° C. After raw data was collected by HPLC-MS, the raw data were respectively peak aligned, extracted, and a metabolome library search was performed to obtain the raw peak table for metabolome analysis.

Figure 1A:
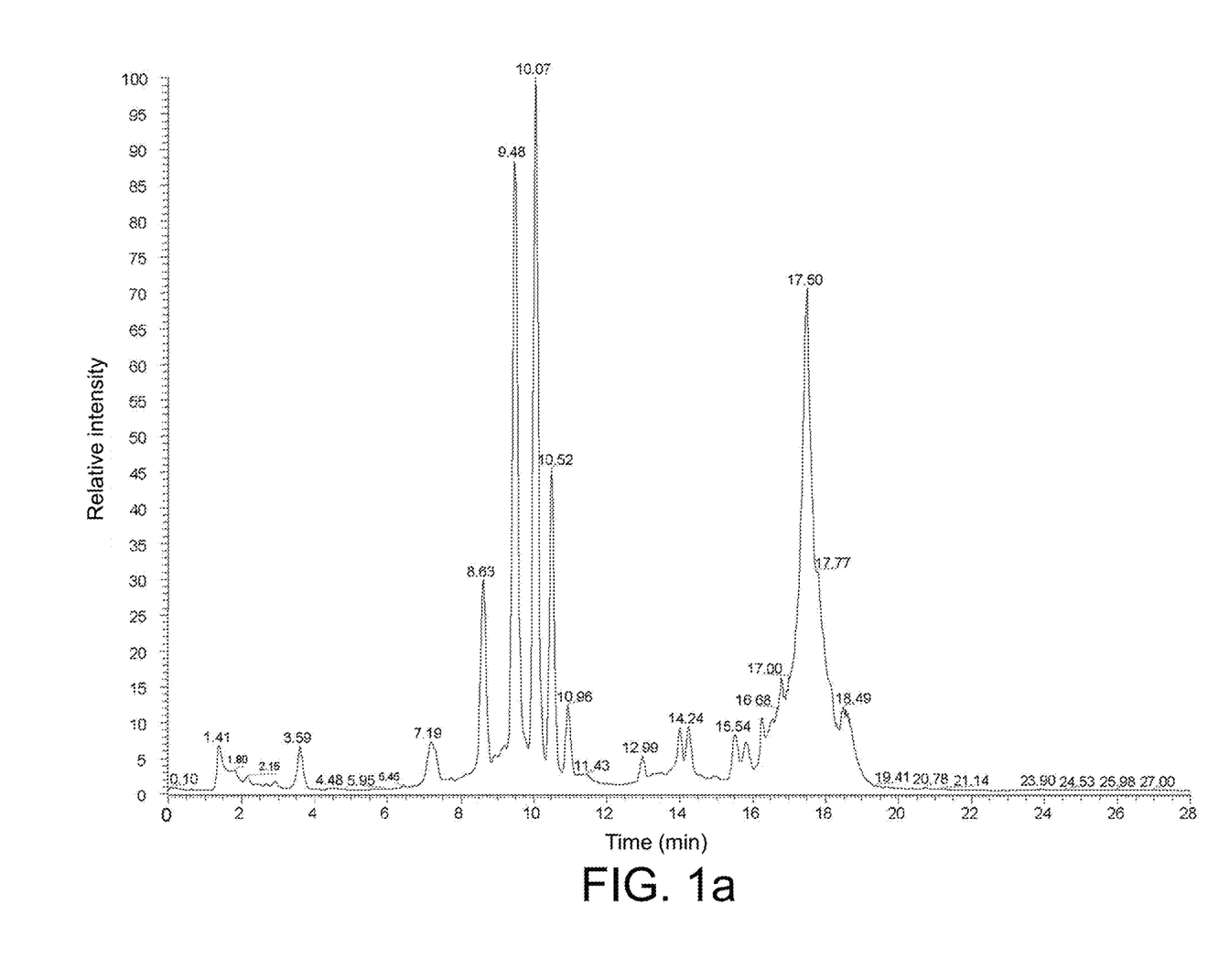
Figure 1B:
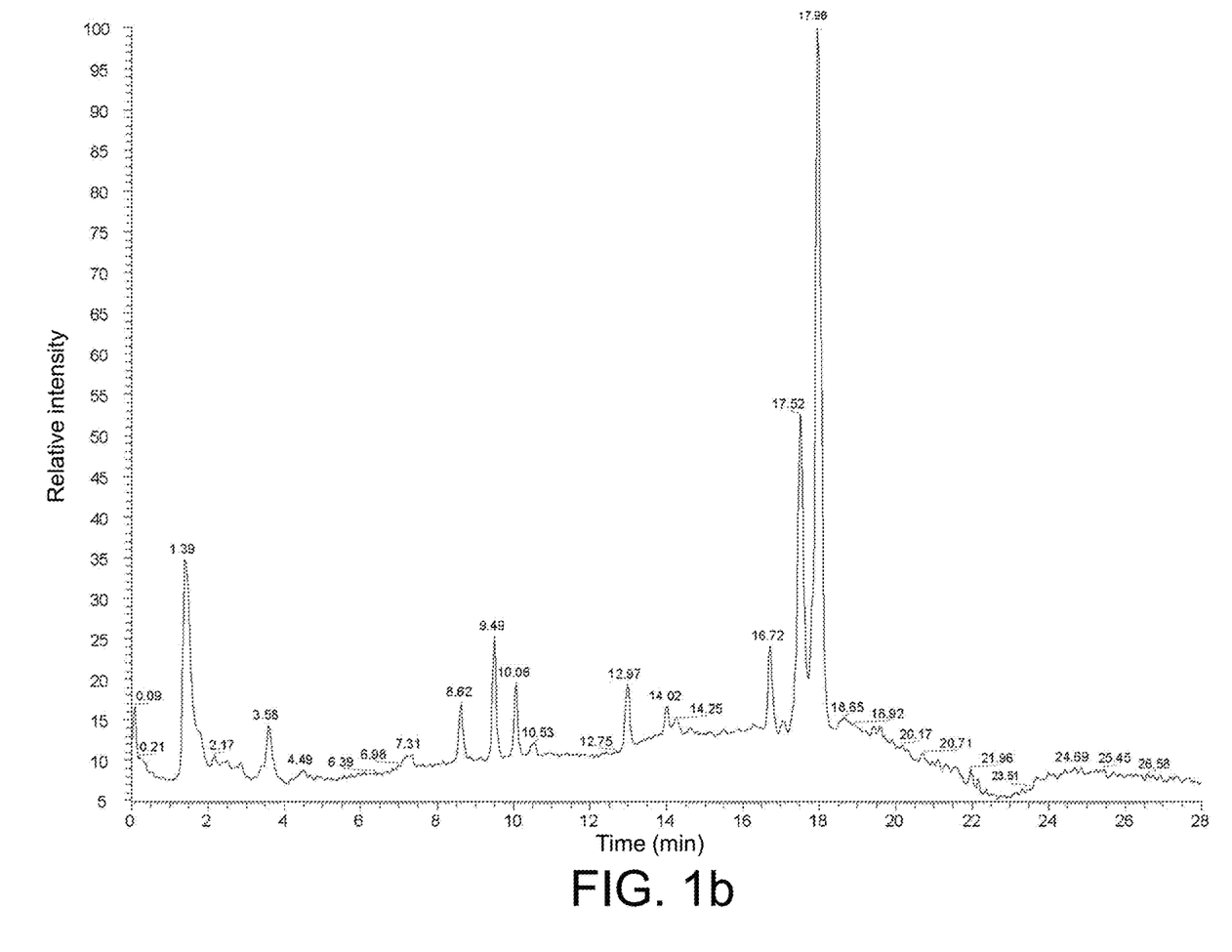

The mass spectrometry chromatogram of the metabolome of Aspergillus flavus cultured at 18° C. and collected by HPLC-MS in the present example is shown in FIGS. 1a~1b. FIGS. 1a~1b illustrate the treatment of Aspergillus flavus cultured at 18° C. with this pretreatment method, polar compounds from 0 to 5 minutes, moderately polar compounds from 5 to 10 minutes, and weakly polar compounds from 10 to 18 minutes, all extracted by pretreatment and chromatographically eluted; in the positive ion acquisition mode and the negative ion acquisition mode, the mass spectrum chromatograms all show the characteristics of many peaks.

Example 2

The pretreatment method for the metabolome analysis of Aspergillus flavus cultured in the Czapek solid medium at 28° C. includes the following steps:

(1) Culture of Aspergillus flavus strain: Aspergillus flavus was inoculated on a Czapek solid medium, and then cultured for 8 to 12 days at 28° C., the spores were washed from the medium using sterile water (containing 0.05 to 0.2% Tween-80); then, the suspension of Aspergillus flavus spores was inoculated into a Sabouraud's liquid medium, the inoculum reached $1 \times 10^5$ to $5 \times 10^5$ cells/ml, and the culture flask was placed on a 25 to 30° C. constant temperature shaker (150 to 250 r/min) and cultured for 5 to 7 days to obtain a sample of Aspergillus flavus;

(2) Quenching of Aspergillus flavus cells using cold glycerol buffer solution combined with rapid filtration:

1. A sample of Aspergillus flavus was rapidly transferred to a centrifuge tube containing a cold glycerol buffer solution quenching agent (formed by mixing glycerol and NaCl solution in a 3:2 volume ratio, <30° C., NaCl solution concentration 13.5 g/L), and the sample to quenching agent volume ratio was maintained between 1:5;

2. The mixture of the sample and the cold glycerol buffer solution quenching agent was rapidly vortexed for 8 to 12 seconds, homogenized, and then the mixture was cooled at −30° C. for 3 to 5 minutes;

3. The mixture was rapidly filtered by vacuum filtration, and the solid sample was collected and freeze-dried for 10 hours after freezing;

(3) Cell disruption and metabolome extraction of Aspergillus flavus: 1 to 2 mL of metabolome extract was taken and added to 100 to 200 mg of the freeze-dried spore sample of step (2), disrupted by ultrasound and extracted for 15 to 20 min, the ultrasonic power was 260 w, centrifuged at 8000 to 10000 rpm for 5 to 10 min, and filtered using a 0.22 μm organic filter membrane to obtain a metabolome extract; the component distribution ratio of the metabolome extract was: volume ratio of MeOH/DCM/ACN/EA/HCOOH=24.5/24.1/24.7/25.7/1;

(4) Metabolome analysis of Aspergillus flavus: the metabolome extract obtained in step (4) was placed in an HPLC-MS system for analysis and detection. The mass spectrometry conditions were: an ion source heating temperature of 250 to 350° C., a spray voltage of 3.5 to 4 Kv in positive ion mode, 3.0 to 3.5 Kv in negative ion mode, a sheath gas of 30 to 40 Arb, an auxiliary gas of 5 to 10 Arb, and an ion transfer capillary temperature of 300 to 320° C. After raw data was collected by HPLC-MS, the raw data were respectively peak aligned, extracted, and a metabolome library search was performed to obtain the raw peak table for metabolome analysis.

Figure 2A:
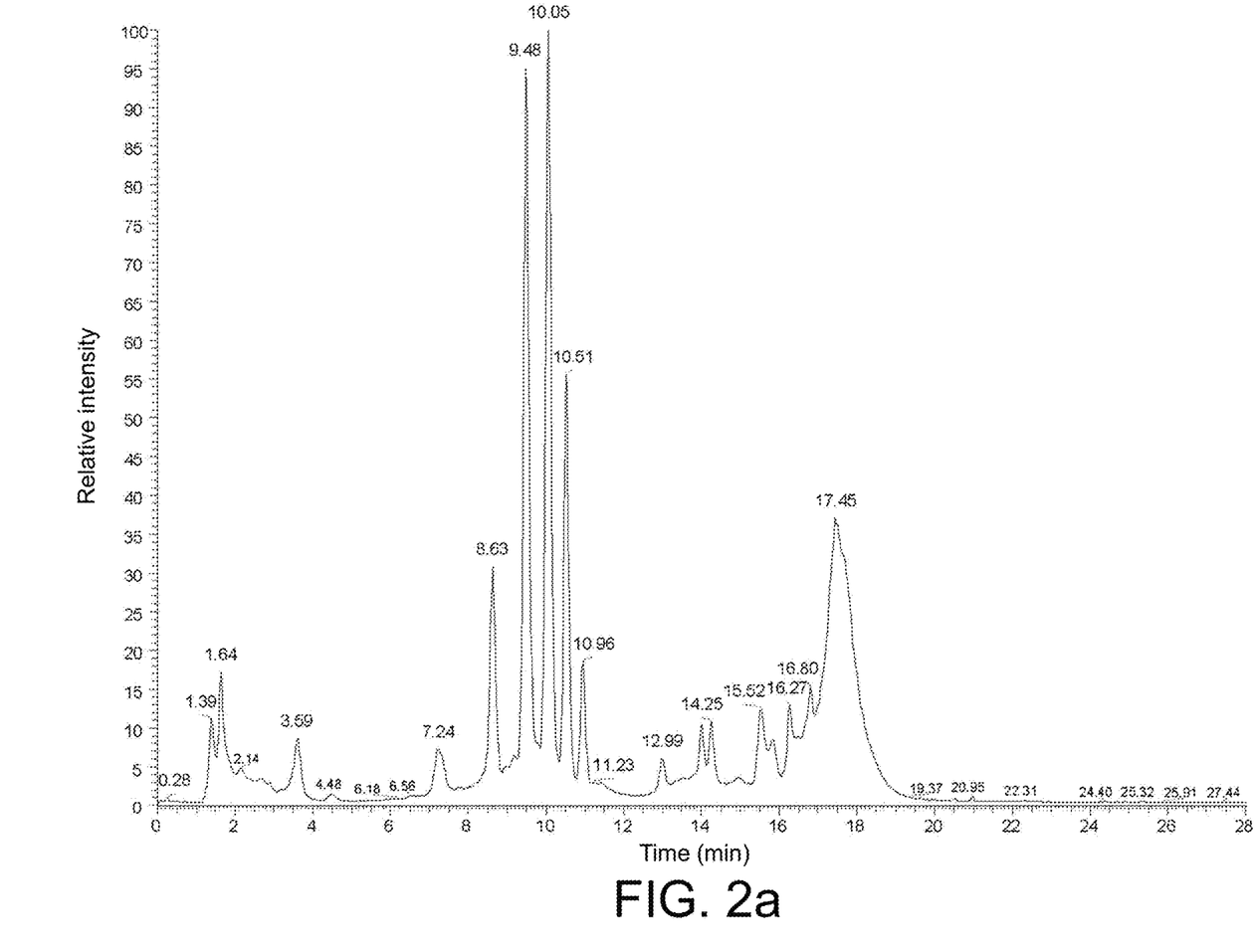
Figure 2B:
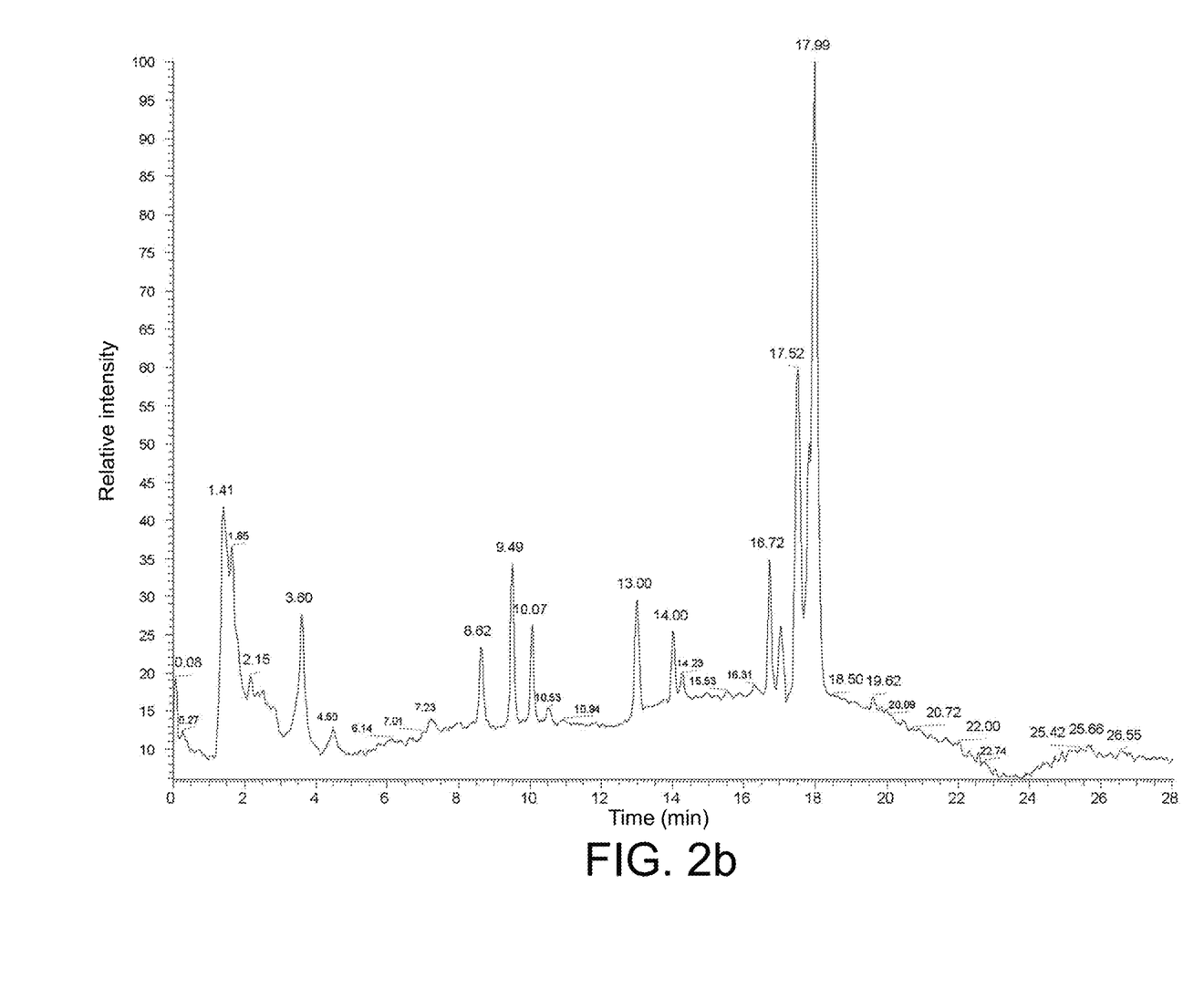

The mass spectrometry chromatogram of the metabolome of the cultured Aspergillus flavus cultured at 28° C. in this example collected by HPLC-MS is shown in FIGS. 2a~2b. FIGS. 2a~2b illustrate the use of the pretreatment method to process Aspergillus flavus cultured at 28° C., polar compounds from 0 to 5 minutes, moderately polar compounds from 5 to 10 minutes, weakly polar compounds from 10 to 18 minutes, all extracted by pretreatment and chromatographically eluted; in the positive ion acquisition mode and the negative ion acquisition mode, the mass spectrum chromatograms all show the characteristics of many peaks.

Example 3

The pretreatment method for the metabolome analysis of Aspergillus flavus cultured in the Czapek solid medium at 38° C. includes the following steps:

(1) Culture of Aspergillus flavus: Aspergillus flavus was inoculated on a Czapek solid medium, and after 8 to 12 days of incubation at 38° C., the spores were washed from the medium using sterile water (containing 0.05 to 0.2% Tween-80); then, the suspension of Aspergillus flavus spores was inoculated into a Sabouraud's liquid medium, the inoculum reached $1 \times 10^5$ to $5 \times 10^5$ cells/ml, and the culture flask was placed on a 25 to 30° C. constant temperature shaker (150 to 250 r/min) and cultured for 5 to 7 days to obtain a sample of Aspergillus flavus;

(2) Quenching of Aspergillus flavus cells using a cold glycerol buffer solution combined with rapid filtration:

1. The sample of Aspergillus flavus was rapidly transferred to a centrifuge tube containing a cold glycerol buffer solution quenching agent (formed by mixing glycerol and NaCl solution in a 2:1 volume ratio, <30° C., NaCl solution concentration 13.5 g/L), and the sample to quenching agent volume ratio was maintained between 1:6;

2. The mixture of the sample and the cold glycerol buffer solution quenching agent was rapidly vortexed for 8 to 12 s, homogenized, and then the mixture was cooled at −20 to −40° C. for 3 to 5 min;

3. The mixture was rapidly filtered by vacuum filtration, and the solid sample was collected and freeze-dried for 8 to 12 hours after freezing;

(3) Cell disruption and metabolome extraction of Aspergillus flavus: 1 to 2 mL of metabolome extract was taken and added to 100 to 200 mg of the freeze-dried spore sample of step (2), disrupted by ultrasound and extracted for 15 to 20 min, the ultrasonic power was 300 w, centrifuged at 8000 to 10000 rpm for 5 to 10 min, and filtered by a 0.22 μm organic filter to obtain a metabolome extract; the component distribution ratio of the metabolome extract was: volume ratio of MeOH/DCM/ACN/EA/HCOOH=24.5/24.1/24.7/25.7/1;

(4) Metabolome analysis of Aspergillus flavus: the metabolome extract obtained in step (4) was placed in an HPLC-MS system for analysis and detection. The mass spectrometry conditions were: an ion source heating temperature of 250 to 350° C., a spray voltage of 3.5 to 4 Kv in positive ion mode, 3.0 to 3.5 Kv in negative ion mode, a sheath gas of 30 to 40 Arb, an auxiliary gas of 5 to 10 Arb, and an ion transfer capillary temperature of 300 to 320° C. After raw data was collected by HPLC-MS, the raw data were respectively peak aligned, extracted, and a metabolome library search was performed to obtain the raw peak table for metabolome analysis.

Figure 3A:
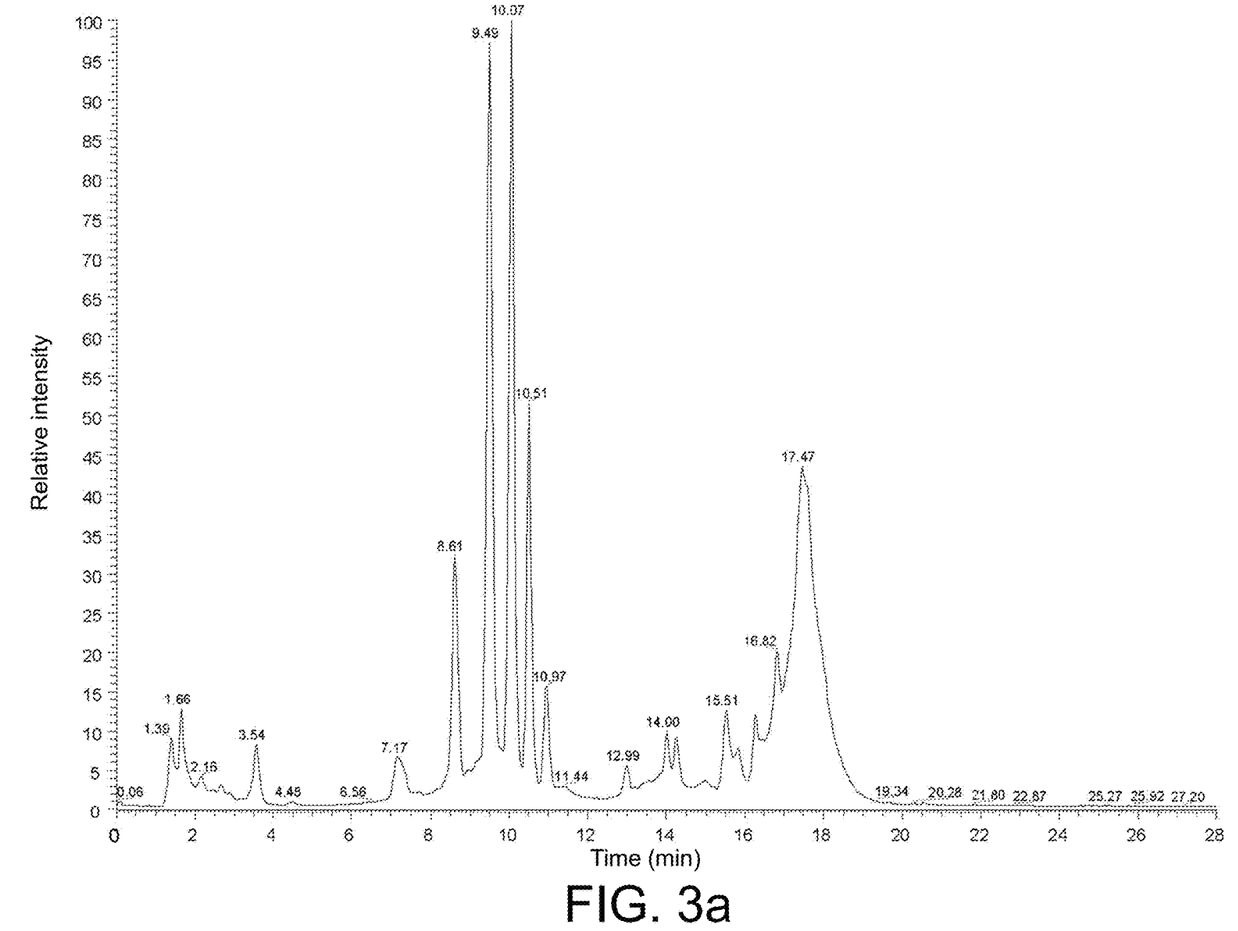
Figure 3B:
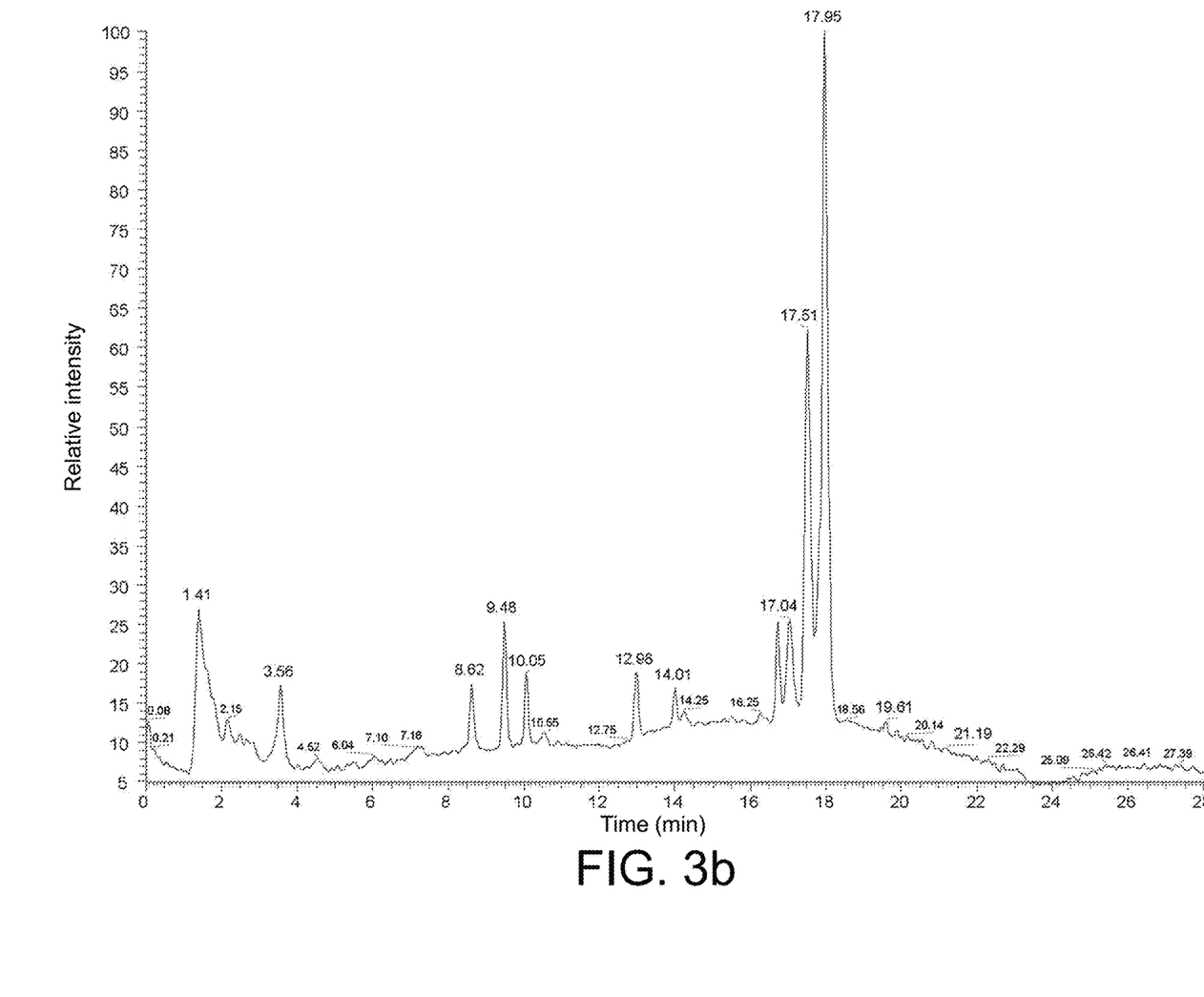

The mass spectrometry chromatogram of the metabolome of Aspergillus flavus cultured at 38° C. and collected by HPLC-MS in this example is shown in FIGS. 3a~3b. FIGS. 3a~3b illustrate the treatment of Aspergillus flavus cultured at 38° C. by this pretreatment method, polar compounds from 0 to 5 minutes, moderately polar compounds from 5 to 10 minutes, and weakly polar compounds from 10 to 18 minutes, all extracted by pretreatment and chromatographically eluted; in the positive ion acquisition mode and the negative ion acquisition mode, the mass spectrum chromatograms all show the characteristics of many peaks.

The invention also compares the method for quenching Aspergillus flavus: in order to obtain a biologically significant metabolomics data, the microbial metabolome sample preparation should firstly quench intracellular and extracellular enzyme activities in time, and the ideal quenching technique should include two basic principles: (1) rapid quenching of enzyme activity, and (2) maintaining cell tissue integrity as much as possible.

Figure 4A:
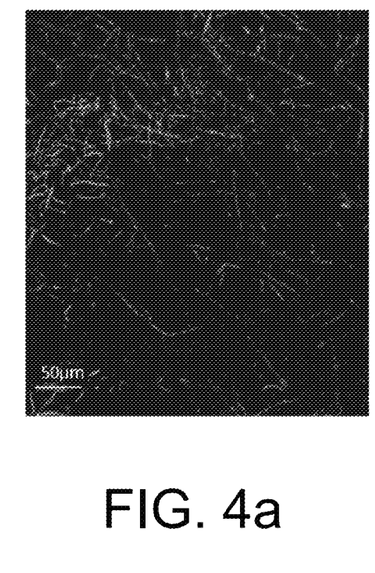
Figure 4B:
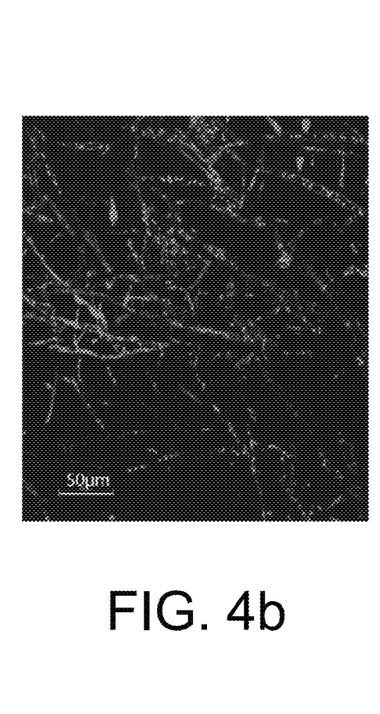
Figure 4C:
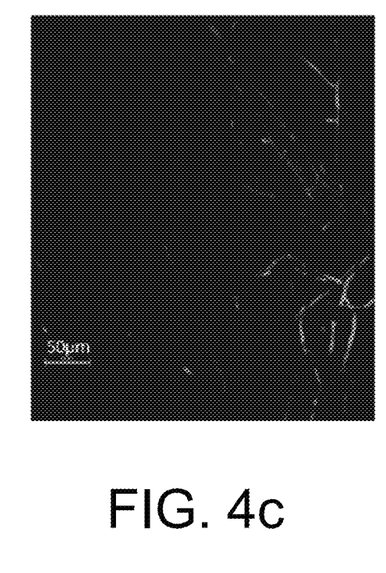

The invention investigates whether three different low-temperature quenching methods cause leakage of filamentous fungal cell metabolomes such as Aspergillus flavus, including liquid nitrogen quenching (<-196° C.), cold methanol (<-30° C.) quenching, cold glycerol buffer solution (<-30° C.) combined with rapid filtration method, and the results are shown in FIGS. 4a~4c, wherein FIG. 4a shows liquid nitrogen quenching, FIG. 4b shows cold methanol quenching, FIG. 4c shows cold glycerol-buffer solution combined with rapid filtration quenching. The principle of propidium bromide (PI) staining is that after the inactivated cell membrane is damaged, PI can enter the cell and bind to intracellular DNA. Under a fluorescence microscope, red light can be observed at the binding site, so cell membrane damage of the cell after treatment with different quenching solvents is studied based on this principle. It can be seen from FIGS. 4a~4c that the method of quenching by cold methanol and liquid nitrogen may cause slight damage to the cell membrane of Aspergillus flavus, causing the outflow of intracellular metabolome, thereby reducing the repeatability and accuracy of the experiment; cold glycerol buffer solution quenching has milder characteristics and does not readily damage cell membrane, and is a promising quenching solvent, but due to the high density of glycerol, the filamentous fungus is light in weight, and is readily suspended such that the filamentous fungus and the quenching solvent are not readily separated by centrifugation. The invention adopts a cold glycerol buffer solution quenching agent combined with rapid filtration separation to overcome the defect that the cold glycerol density is large and Aspergillus flavus floats on the upper layer and is not readily centrifuged. In the invention, cold glycerol buffer quenching combined with rapid filtration method is used as a whole component metabolomics sampling quenching method for Aspergillus flavus.

It is apparent that the above-described examples are merely illustrative of the examples, and are not intended to limit the examples. Other variations or modifications of the various forms may be made by those skilled in the art in light of the above description. There is no need and no way to exhaust all of the implementations. Thus, the obvious changes or variations that are derived are still within the scope of the invention.

What is claimed is:

1. A pretreatment method for detecting metabolomics of Aspergillus flavus by LC-MS, comprising the following steps:
   (1) culturing a strain of Aspergillus flavus: after culturing Aspergillus flavus in a solid medium, washing spores from the solid medium with a sterile water and then inoculating the spores into a liquid medium for propagation to obtain a sample of Aspergillus flavus;
   (2) quenching Aspergillus flavus: adding the sample of Aspergillus flavus obtained from step (1) to a cold glycerol buffer solution quenching agent, rapidly mixing and vortexing, homogenizing, then cooling under low temperature conditions, and then rapidly filtering a mixture by vacuum filtration, and collecting a solid sample, and freeze-drying the solid sample to obtain a cell sample of Aspergillus flavus;
   (3) disrupting a cell membrane of Aspergillus flavus and extracting a metabolome: disrupting the cell sample of Aspergillus flavus obtained by freeze-drying in step (2) and performing an extraction process using a metabolome extract, and then centrifuging and membrane-filtering to obtain a metabolome extraction solution for the metabolomics of Aspergillus flavus analysis by LC-MS detection,
   wherein the metabolome extract of step (3) is formed by mixing methanol, dichloromethane, acetonitrile, ethyl acetate, and formic acid in a volume ratio of 20 to 30:20 to 30:20 to 30:20 to 30:1 to 2.

2. The pretreatment method for detecting the metabolomics of Aspergillus flavus by LC-MS of claim 1, wherein the cold glycerol buffer solution quenching agent in step (2) is prepared by mixing glycerol and a NaCl solution in a volume ratio of 1:1 to 2:1.

3. The pretreatment method for detecting the metabolomics of Aspergillus flavus by LC-MS of claim 1, wherein the cold glycerol buffer solution quenching agent is precooled to -30° C. or less for use, and a concentration of the NaCl solution is 10 to 15 g/L.

4. The pretreatment method for detecting the metabolomics of Aspergillus flavus by LC-MS of claim 1, wherein a volume ratio of the sample of Aspergillus flavus and the cold glycerol buffer solution quenching agent in step (2) is 1:4 to 1:6.

5. The pretreatment method for detecting the metabolomics of Aspergillus flavus by LC-MS of claim 1, wherein the cooling under low temperature conditions in step (2) is as follows: cooling the mixture at -20 to -40° C. for 3 to 5 minutes.

6. The pretreatment method for detecting the metabolomics of Aspergillus flavus by LC-MS of claim 1, wherein in step (3), the metabolome extract is added in an amount of 1 to 2 mL based on 100 to 200 mg of the cell sample of Aspergillus flavus.

7. The pretreatment method for detecting the metabolomics of Aspergillus flavus by LC-MS of claim 1, wherein the extraction process in step (3) is an ultrasonic disruption extraction, an ultrasonic power is 240 W to 300 W, and an ultrasonic disruption extraction time is 15 to 20 minutes.

8. The pretreatment method for detecting the metabolomics of Aspergillus flavus by LC-MS of claim 1, wherein a time of the freeze-drying in step (2) is 8 to 12 hours, a centrifugal speed in step (3) is 8000 to 10000 rpm, and a centrifugal time is 5 to 10 minutes; a membrane used in the membrane-filtering is a 0.22 μm organic membrane.

9. The pretreatment method for detecting the metabolomics of Aspergillus flavus by LC-MS of claim 1, further comprising step (4):

analysing the metabolomics of Aspergillus flavus: placing the metabolome extraction solution obtained in step (3) in an HPLC-MS system for analysis and detection, and then performing to analyze the metabolomics of Aspergillus flavus according to an obtained spectrum; mass spectrometric conditions detected by the HPLC-MS system in step (4) are: an ion source heating temperature of 250 to 350° C., a spray voltage of 3.5 to 4 Kv in a positive ion mode, 3.0 to 3.5 Kv in a negative ion mode, a sheath gas of 30 to 40 Arb, an auxiliary gas of 5 to 10 Arb, and an ion transfer capillary temperature of 300 to 320° C.

* * * * *